US00PP11603P

United States Patent [19]

Avent

[11] Patent Number: Plant 11,603

[45] Date of Patent: Oct. 24, 2000

[54] HOSTA PLANT NAMED 'TATTOO'

[76] Inventor: Tony Avent, 9241 Sauls Rd., Raleigh, N.C. 27603

[21] Appl. No.: 09/222,279

[22] Filed: Dec. 28, 1998

[51] Int. Cl.[7] ..... A01H 5/00

[52] U.S. Cl. ..... Plt./353

[58] Field of Search ..... Plt./353

*Primary Examiner*—Howard J. Locker
*Assistant Examiner*—Michelle Kizilkaya
*Attorney, Agent, or Firm*—C. A. Whealy

[57] ABSTRACT

A distinct cultivar of Hosta plant named 'Tattoo', characterized by its small, rounded golden green leaves with a distinct darker green maple leaf-shaped outline or "tattoo" in the center of the leaf; relatively compact plant habit; and light lavender flowers that are positioned above the foliage on strong and erect peduncles.

1 Drawing Sheet

BACKGROUND OF THE INVENTION

The present invention relates to a new and distinct cultivar of Hosta plant, botanically known as Hosta hybrid, and hereinafter referred to by the cultivar name Tattoo.

The new cultivar was discovered by the Inventor in Raleigh, N.C., as a naturally-occurring leaf mutation of a plant of the nonpatented Hosta hybrid cultivar Little Aurora in 1993. The parent cultivar is described as a compact Hosta with golden cordate-shaped leaves and is derived from a cross of the nonpatented Hosta hybrid cultivars *Tokudama aureonebulosa* and *Golden Waffles*.

Asexual propagation of the new cultivar at Raleigh, N.C., by division and by tissue culture, has shown that the unique features of this new Hosta plant are stable and reproduced true to type in successive generations of asexual propagation.

The new Hosta has not been observed under all possible environmental conditions. The phenotype may vary somewhat with variations in environment such as temperature and light intensity, without, however, any variance in genotype.

SUMMARY OF THE INVENTION

The following traits have been repeatedly observed and are determined to be the unique characteristics of 'Tattoo'. These characteristics in cimbination distinguish 'Tattoo' as a new and distinct cultivar:

1. Small, rounded golden green leaves with a distinct darker green maple leaf-shaped outline or "tattoo" in the center of the leaf.

2. Relatively compact plant habit.

3. Light lavender flowers that are positioned above the foliage on strong and erect peduncles.

The new Hosta can be compared to its parent cultivar, the cultivar Little Aurora. Plants of the new Hosta have a distinct green maple leaf outline on the leaf whereas plants of the parent cultivar do not exhibit the maple leaf outline and leaves are golden in color. In addition, plants of the new Hosta are slightly more compact than plants of the parent cultivar.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a plant 'Tattoo' planted in a cultivated area prior to flowering. Leaf colors in the photograph may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe six-month old plants grown in one-liter containers in Raleigh, N.C., under 63 percent shade with day and night temperatures ranging from 27 to 35° C. and 16 to 27° C., respectively.

Botanical classification: Hosta hybrid cultivar Tattoo.

Parentage: Naturally-occurring mutation of Hosta hybrid cultivar Little Aurora, not patented.

Propagation:

*Method.*—By division and by tissue culture.

*Time to initiate roots from division.*—About 2 to 4 weeks.

*Rooting habit.*—Freely branching, numerous fleshy roots.

Plant description:

*Plant shape.*—Mounding, dome-shaped, symmetrical.

*Growth habit.*—Initially upright becoming outwardly arching as leaves develop. Moderate to freely clumping. Appropriate for one-liter containers.

*Crop time.*—Usually about six months are required to produce a finished one-liter plant under North American conditions.

*Plant vigor and growth rate.*—Moderate to high.

*Plant size.*—A finished one-liter plant will be about 15.25 cm from soil level to top of leaf plane and about 25.5 cm wide.

*Foliage description.*—Shape: Initially ovate becoming more rounded with development with apiculate to acute apex and cordate base. Margin: Entire. Texture: Leathery, glabrous, rugose. Length: About 7.5 cm. Width: About 7.5 cm. Venation pattern: Camptodromous Color: Golden green-colored leaves with darker green maple leaf-shaped outline in the center of the leaf, about 1.25 to 2 cm interior to the leaf margin; maple leaf-shaped outline surrounded by green outer area. Upper surface: Iridescent, golden green center, greener than 151A; maple leaf-shaped outline darker green, 146A to 147A; area surrounding maple leaf-shaped outline to margin, green, close to 146A. Lower surface: Iridescent, golden green center, much greener than 151A; maple leaf-shaped outline darker green, 146A; area surrounding maple leaf-shaped outline to margin, green, close to 146A. Petiole length: About 3.75 cm. Petiole color: Upper surface: 144A. Lower surface: 144A.

Flower description:

*Flower arrangement.*—At least 20 single flowers with six fused petals arranged on a terminal scapose, bractless raceme. Flower stems arise from leaf axils. Typically one flower stem per plant. Flowering recurrent from mid-July through mid-August in the Northern Hemisphere.

*Flower shape.*—Star-shaped.

*Flower diameter.*—About 1.5 cm.

*Flower depth* (*height*).—About 2.75 cm.

*Persistence.*—At least 1 week for individual blooms and at least 3 weeks for raceme.

*Petals.*—Arrangement: Three interior, three exterior, fused. Apex: Acute. Margin: Entire. Texture: Smooth, satiny. Length: About 2.75 cm. Color, upper and lower surfaces: Very light lavender, close to 75D.

*Scape.*—Aspect: Strong and erect. Length: About 25.5 cm. Flowers held about 7.5 cm above the foliage. Diameter: About 6 mm. Color: Green.

*Scape bracts.*—None observed.

*Reproductive organs.*—Androecium: Stamen number: Usually six. Anther size: About 6 mm. Pollen color: Yellow. Gynoecium: Stigma color: White. Style color: White. Style length: About 2.5 cm.

Disease resistance: Resistance to pathogens common to Hosta has not been observed.

Seed development: Seed development has not been observed.

It is claimed:

1. A new and distinct cultivar of Hosta plant named 'Tattoo', as illustrated and described.

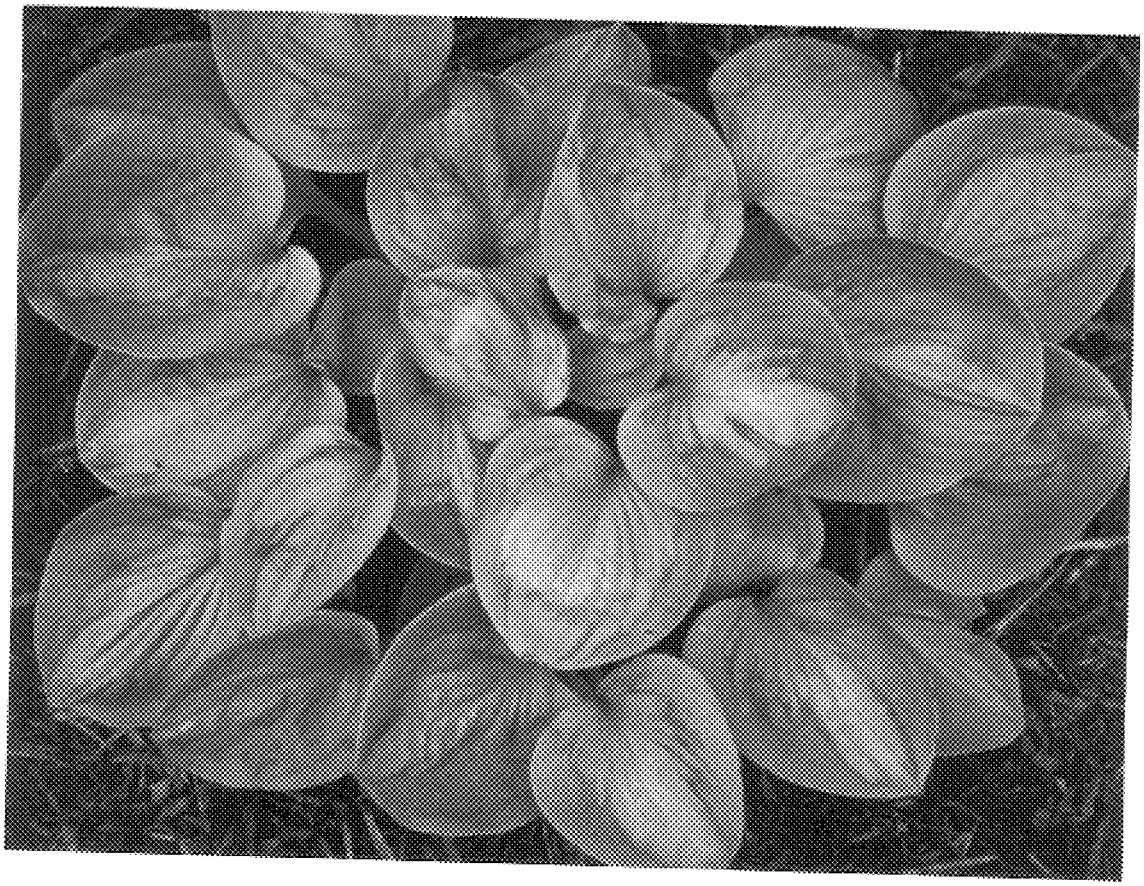

* * * * *